United States Patent [19]

Errede et al.

[11] 4,373,519
[45] Feb. 15, 1983

[54] COMPOSITE WOUND DRESSING

[75] Inventors: Louis A. Errede, North Oaks; James D. Stoesz, St. Paul, both of Minn.; George D. Winter, deceased, late of St. Paul, Minn., by Jenny Upton, personal representative

[73] Assignee: Minnesota Mining and Manufacturing Company, St. Paul, Minn.

[21] Appl. No.: 277,990

[22] Filed: Jun. 26, 1981

[51] Int. Cl.³ .................... A61L 15/00; A61F 13/00
[52] U.S. Cl. ................................. 128/156; 128/296
[58] Field of Search ...................... 128/155–156, 128/284, 287, 290 R, 296

[56] References Cited

U.S. PATENT DOCUMENTS

| | | | |
|---|---|---|---|
| 2,893,105 | 7/1959 | Lauterbach | 128/156 |
| 2,910,763 | 11/1959 | Lauterbach | 128/156 |
| 3,731,683 | 5/1973 | Zaffaroni | 128/156 |
| 3,886,941 | 6/1975 | Duane et al. | 128/156 |
| 3,888,257 | 6/1975 | Cook et al. | 128/296 |
| 3,901,236 | 8/1975 | Assarsson et al. | 128/290 R |
| 3,903,268 | 9/1975 | Balassa | 128/156 |
| 3,908,650 | 9/1975 | Dunshee et al. | 128/156 |
| 3,949,130 | 4/1976 | Sabee et al. | 128/296 |
| 4,058,124 | 11/1977 | Yen et al. | 128/290 R |
| 4,153,661 | 5/1979 | Ree et al. | 264/120 |
| 4,192,727 | 3/1980 | Ward | 128/290 R |
| 4,203,435 | 5/1980 | Krull et al. | 128/156 |

FOREIGN PATENT DOCUMENTS 1454055 1/1974 United Kingdom.

OTHER PUBLICATIONS

Åberg et al., [Ålberg, M., Hedner, U., Jacobson, S. and Rothman, U., "Fibrinolytic Activity in Wound Secretion", Scand. J. Plast. Recon. Surg. 10, pp. 103–105, (1976)].

Primary Examiner—C. Fred Rosenbaum
Attorney, Agent, or Firm—Cruzan Alexander; Donald M. Sell; Lorraine R. Sherman

[57] ABSTRACT

A composite wound dressing, optionally having controlled permeability, is highly absorbent toward blood and exudate and comprises a polytetrafluoroethylene fibril matrix, hydrophilic absorptive particles enmeshed in the matrix, and, optionally, a partially occlusive film coated on one surface of the matrix.

18 Claims, 1 Drawing Figure

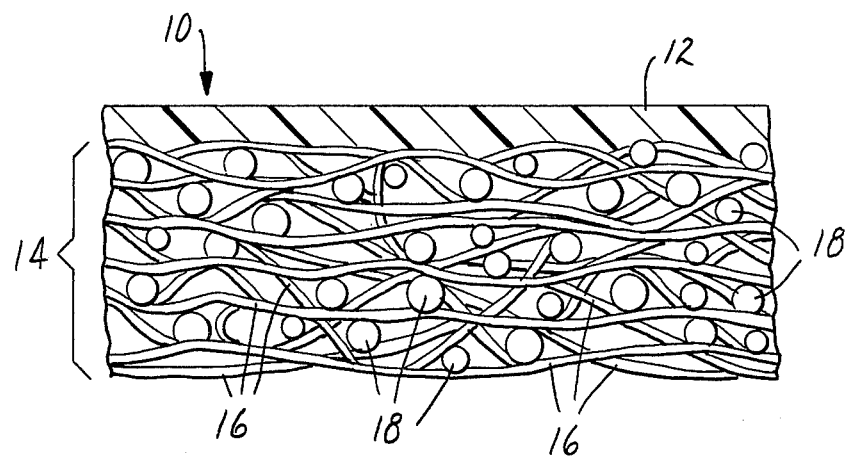

COMPOSITE WOUND DRESSING

TECHNICAL FIELD

The present invention relates to a composite wound dressing which is highly absorbent towards blood and exudate, yet non-adherent to the wound surface, having controlled water vapor permeability.

BACKGROUND ART

It has been recognized in the prior art that a satisfactory wound dressing creates a suitable microclimate for rapid and effective healing. A good wound dressing prevents dehydration and scab formation, is permeable to oxygen, is sterilizable, absorbs blood and exudate, protects against secondary infection, supplies mechanical protection to the wound, is non-adherent, is non-toxic, is non-allergenic or sensitizing, does not shed loose material into the wound, conforms to anatomical contours, resists tearing, resists soiling, is not inflammable, has constant properties in a range of temperatures and humidities encountered in use, has long shelf life, has small bulk, is compatible with medicaments, and is economical.

Layered dressings are known in the art. U.S. Pat. No. 4,203,435 discloses a five-layered wound dressing having two permeable, non-adherent outer layers, the next two layers being cellulosic fiber absorbent layers, and the inner-most layer comprising a powder of modified starch. U.S. Pat. No. 3,888,257 provides a layered disposable, absorbent article for management of body fluid flow, in which a central zone of a matrix of fiberized wood pulp incorporates a three-dimensional dispersion of hydrocolloid polymer particles.

Great Britain Pat. No. 1,454,055 discloses a preparation, such as a bandage, for treating a fluid-discharging skin surface, which comprises a water-insoluble hydrophilic macromolecular swellable material such as crosslinked dextran, carboxymethyldextran, starch or hydroxyethyl starch for absorbance of low molecular weight constituents of blood plasma in admixture with a dermatologically suitable carrier. The swellable material may be dextran, or a derivative thereof, and the carrier may comprise fibrous material. This patent discloses no fibrous materials having submicron diameters nor does it disclose a partial moisture barrier in the preparation to prevent the wound from drying out.

A crosslinked dextran derivative which is sold by Pharmacia of Sweden under the tradename "Debrisan", is primarily used as a wound treating powder. Pharmacia's trade literature on Debrisan ® asserts the following advantages for the use of the powder: "continuously absorbs wound exudate and bacteria, cleanses the wounds, prevents crust formation, reduces inflammation and oedema and does not cause sensitization". The trade literature which states that no side effects have been reported also gives the following limitations on the product: "(1) do not leave Debrisan ® for more than 24 hours on wounds with a very low exudation rate as it may dry and form a crust which may be difficult to wash off, (2) occlusive dressings may lead to maceration of skin around the wound under treatment, (3) when deep infected wounds are treated, care must be taken to wash Debrisan ® from the depths of the wound, and (4) no side effects have been reported. Warning: Debrisan ® spillage can render surfaces very slippery. Clear spillings promptly." Thus, it appears that although the dextran derivatives have excellent absorptive capacities, there are problems associated with their use relating to moisture loss, adhesion, contamination of the wound, and handling hazards.

DISCLOSURE OF INVENTION

The present invention overcomes some of these problems by providing a composite wound-dressing which is a sheet material comprising:
(a) a polytetrafluoroethylene (PTFE) fibril matrix;
(b) 0.5 to 10 parts of hydrophilic absorptive particles per part of PTFE by weight enmeshed in said matrix, the absorptive particles having absorptive capacity greater than 0.5 grams of water per gram of dry particles; and
(c) optionally, a partially occlusive film coated on one surface of said matrix.

By "occlusive film" is meant a layer of material having controlled permeability or porosity.

When the partially occlusive film is present, such a coating has controlled permeability and it reduces the rate of evaporation of moisture out of the dressing to the atmosphere thereby reducing the tendency for formation of a hardened scab over the wound. Scab formation is undesirable because it retards healing and enhances scar formation. In addition, by slowing the moisture loss from the wound surface, the moisture barrier imparts to the wound dressing of the instant invention superior non-adherent properties.

The absorptive particles of the present invention are thoroughly enmeshed in the PTFE fibrils so that substantially all of the particles are contained in the fibrils and do not slough in the wet or dry state. Contamination of the wound from particulate matter originating in the dressing is thereby prevented.

The composite wound dressing of the present invention has many desirable characteristics. For example, it provides an ideal microclimate for healing in that it is highly permeable, thereby allowing oxygen to permeate the membrane. The bandage is sterilizable. The composite is a good absorbent for blood and exudate (see Example 2) and does not adhere to the wound surface. These properties exist because the absorptive particles are not in direct contact with the wound but are separated therefrom by an intertwining coat of polytetrafluoroethylene fibrils. The dressing is particularly advantageous in that it need not be changed every day. The wound dressing affords rapid absorption of exudate and thereby draws bacteria away from the wound, helping to protect against wound sepsis, as will be discussed below. Dressings of the present invention can provide water absorptive capabilities as high as about 40 grams of water per gram of dressing. When a partially occlusive film is present as the outermost layer on the PTFE fibril matrix, the moisture transmission is controlled so that the wound stays moist enough to prevent scab formation and adherence of the dressing to the wound surface and to permit rapid epidermal wound healing.

The composite wound dressing of the present invention consisting of a PTFE fibril matrix in which absorptive particles are enmeshed, but which has no moisture controlling coating, also has many of these desirable characteristics. Such dressings are most useful in treating wounds which produce large amounts of exudate, for example highly infected wounds. In such a situation, it is desirable to change the dressing frequently, since the absorptive capacity of the dressing tends to be quickly exhausted. However, rapid evaporation of moisture prolongs the length of time the dressing remains absorbent on the wound. Thus, dressings both with and without moisture evaporation retarding coatings are useful, depending on the rate at which a wound is producing exudate. It is most desirable to use a dressing which absorbs exudate at approximately the rate the wound is producing exudate to prevent either dehydration of the wound or excessive accumulation of exudate on the wound surface.

The composite dressing, a chamois-like material, is very comfortable yet tough enough to provide some protection against the abrasive and penetrating effects of foreign objects. It maintains its physical integrity under normal handling conditions, is not soiled due to its chemical inertness and low surface tension, does not physically or chemically degrade (i.e., it has good shelf life) and the chemical and physical properties are not adversely affected by changes in temperature from $-20°$ C. to $120°$ C. Polytetrafluoroethylene is presented at the surface directly adjacent to the wound. The absorptive particles are not on the surface of the composite but are strongly enmeshed in tough PTFE fibrils. Therefore, there is very little chance that any absorptive particles will slough off and get into the wood. The PTFE fibrillated surface is not rendered adhesive by other materials because it is non-absorptive and non-wetted due to its unusually low surface tension despite the fact that the composite is very hydrophillic. In addition, PTFE is non-toxic, non-allergenic and nonsensitizing.

In summary, the physical properties of the wound dressing are considerably superior to those of the prior art.

BRIEF DESCRIPTION OF DRAWING

The drawing shows a cross-sectional view, greatly enlarged, of a composite wound dressing of the present invention.

DETAILED DESCRIPTION

The present invention provides a composite wound-dressing which is a sheet material, optionally having controlled porosity, comprising:
(a) a polytetrafluoroethylene fibril matrix;
(b) 0.5 to 10 parts of hydrophilic absorptive particles per part of PTFE by weight enmeshed in said matrix, said absorptive particles having absorptive capacity greater than 0.5 grams of water per gram of dry particle; and
(c) optionally, a partially occlusive film coated on one surface of the matrix;
wherein substantially all of the hydrophilic absorptive particles are unavailable for sloughing.

FIG. 1 shows one embodiment of a composite wound dressing 10 according to the present invention having occlusive film 12 coated on one surface of the matrix 14 of PTFE fibrils 16 in which are enmeshed hydrophilic absorptive particles 18.

To prepare the composite wound-dressing the hydrophilic particles are incorporated into a PTFE emulsion to form a paste, which is subjected to a great amount of shear causing the PTFE to fibrillate and enmesh the particles into a fibrillar matrix. There are many processes of fibrillating PTFE and virtually all non-sintering processes are adaptable to the method of making the composite of the instant invention. The most suitable, however, is that described by Ree et al. in U.S. Pat. No. 4,153,661, and is hereby incorporated by reference.

Basically, the fibrillation involves the formation of a paste of water swollen particulate material and PTFE particles, intensive mixing at $50°$ to $100°$ C., biaxial calendering, and a drying step. This results in a membrane with PTFE fibrils having a thickness in the range of about 0.025 to 0.5 micrometers.

The size of the absorbent-type particles are within a broad range of 0.1 to 300 micrometers when dry. Preferably, the particle size range of the hydrophilic polymer absorbent is 1.0 to 80 micrometers. The particles which are insoluble in a wound environment have an absorptive capacity greater than 0.5 (i.e., in the range of 0.5 and 40 grams) of water per gram of dry particles.

Because of its high absorptive capacity, the wound dressing may be used to cleanse the surfaces of contaminated or infected wounds. Such wounds include traumatic wounds, cuts, lacerations and abrasions, burns, indolent wounds, pressure sores, and ulcers which may be contaminated with foreign matter, dead tissue, and microorganisms such as bacteria and fungi. For this cleansing purpose dressings of the instant invention may be removed and replaced as often as necessary to remove contaminating material, and then a final similar dressing may be left in place undisturbed on the cleansed surface until the wound heals. Alternatively, if the wound is too deep to heal spontaneously, after cleansing the wound surface in the above manner, it may be grafted. It is to be noted that some of the cleansing action is brought about by the activities of cells, (e.g., leukocytes and macrophages) in the tissues of the body, aided by appropriate conditions of hydration and oxygen availability brought about by the dressing. The breakdown products are removed by the absorbent in the dressing, thus completing the cleansing process. A particular advantage of the wound dressing having a partially occlusive film of the instant invention compared with other means of wound debridement is that the controlled wound environment provided herein is an intrinsic part of the dressing by reason of its controlled permeability and, therefore, there is no danger that the wound is made too soggy or is dehydrated, both of which conditions adversely affect wound repair.

The hydrophilic absorbent may be particles comprised of alginic acid, polyacrylate-cellulose graft copolymer, collagen, chitin, chitosan, clay, casein, zein, dextran, carboxymethyldextran, starch, modified starch, hydroxyethyl starch, hydrolyzed polyacrylonitrile, starch-methacrylonitrile polymer, polyacrylamide, hydrolyzed polyacrylamide (Separan ® AP-30 from the Dow Chemical Co.), cellulose, carboxymethylcellulose, and derivatives or mixtures of the aforementioned materials. The most preferred material is a crosslinked dextran derivative, having a water absorptive capacity between 2 g and 10 g of water per gram of dry material. The thickness of dressings providing satisfactory volume absorption is in the range of 0.1 to 10 mm, preferably in the range of 0.25 mm to 5 mm.

Hydrophilic absorbent particles may be admixed with inert less-absorptive diluent particulates which range in size from 0.1 to 100 micrometers to improve the feel and handling characteristics of the composites and to facilitate their manufacture. Examples of diluent particles include powdered polymers such as polyethylene, polypropylene, and polystyrene, kaolin, talc, silica, bentonite, and vermiculite.

The particulate material accounts for from 40 to 90%, and preferably 80–90%, by weight of the total composition, of which up to 50% can be inert diluent particles. The most preferred amount of total particulates is about 85% by weight.

As noted above, if the uncoated PTFE-absorptive particulates composite membrane is used as a wound-treating material for extended periods of time, there is a tendency for formation of a hardened scab over the wound due to excessive moisture transmission out of the dressing to the atmosphere. Thus, to render the dressing satisfactory for long periods, evaporation rates must be reduced by means of a coating on one side of the bandage. No coating is required for short (1–4 hours) application times, especially for wounds which produce large amounts of exudate.

The surface coating must be flexible and not totally occlusive, e.g., a film which controls the evaporative loss to a rate which allows low levels of moisture to remain in the bandage. Coatings which allow water transmission through the wound dressing in the range of 240 to 2400 g/m$^2$/24 hours, in vivo, measured by this desiccant method, 37° C., 75% relative humidity, modified ASTM E96-66 (reapproved 1972), Procedure A, are useful. The thickness of dressings providing these rates of water transmission is generally in the range of 0.1 to 5 millimeters, the thickness of the coating on the surface of the dressing being in the range of 2 to 200 microns. Suitable coatings can be achieved with any material that will restrict the passage of water molecules, including silicone, urethane, and acrylate polymers.

Medicaments which may be useful in promoting wound healing or reducing infection of wounds can be incorporated in the composite wound dressings. These can include but are not limited to antibacterial agents, such as the penicillins, the aminoglycosides, iodine and other well known antibiotics useful in reducing infection; antifungal agents such as nystatin and undecylenic acid; hemostatic agents such as microcrystalline cellulose, chitosan, thrombin, and fibrin; and, wound-healing promoting agents such as epidermal growth factor, ascorbic acid, collagen, and aluminum salts such as aluminum acetate and aluminum chlorohydrate.

Objects and advantages of this invention are further illustrated by the following examples, but the particular materials and amounts thereof recited in these examples, as well as other conditions and details, should not be construed to unduly limit this invention.

EXAMPLE 1-Preparation and Characterization of Composite Dressing Materials

The general procedures disclosed in U.S. Pat. No. 4,153,661, mentioned above, were used to prepare the composite dressing materials. The specific methods used were as follows.

Fifty grams of Sephadex ® G-25-80 (crosslinked dextran derivative, particle size 20–80 microns, available from Sigma Chemical Co., St. Louis, MO) and 50 gm of water were mixed in a one-liter beaker. The Sephadex ® absorbed all the water and swelled from 60 cc to a total volume of 210 cc. Sixty grams of water and 20 grams of polytetrafluoroethylene (PTFE) resin dispersion (Teflon ® 30B, Dupont) were mixed and added to the swollen Sephadex ® in 10 ml portions with intermittent vigorous stirring. After these ingredients had been thoroughly mixed, a semi-coherent material was formed with enough physical integrity to allow the entire contents to be removed from the beaker as a single mass.

The above mass was passed through two rollers kept at 50° C. and spaced about 0.4 cm apart to give a strip of cohesive material which barely supported its own weight of dimensions approximately 14 cm×0.4 cm×42 cm. The resulting strip was folded to three thicknesses or a material having dimensions of 14 cm×1.2 cm×14 cm and then passed through the rollers after a 90° rotation from the previous pass. The cyclic process of three-layer folding and re-rolling in the direction 90° from the direction of the preceding pass was repeated a total of 14 times to give a tough, strong, flat piece of material of dimensions 14 cm×0.4 cm×42 cm. The material was then calendered along the long axis through a set of ten rollers which were spaced at successively smaller distances apart to give a continuous ribbon of dimensions 14 cm×0.04 cm×480 cm. The ribbon was folded to give a 32-layered piece of dimensions 14 cm×1.3 cm×15 cm. The 32-layered piece was then calendered as before along the 14 cm axis (90° from the calendering direction used previously) to give a ribbon of dimensions 15 cm×0.05 cm×350 cm. By calendering using varying spaced rollers, different degrees of compaction of the mass could be obtained and various thicknesses of ribbon, as desired, realized. The calendered sheet of material was washed in a water bath and then allowed to dry in air for 48 hours. It was then stretched to a width of 20 cm to give it a softer, more comfortable feel. The resulting dressing material was then coated with a semi-occlusive polymeric film.

The semi-occlusive film was prepared from nine grams of a vinyl functional polydimethylsiloxane material (3M)

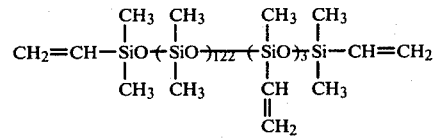

containing 50 ppm of platinum catalyst, (pyridine) PtCl$_2$(C$_2$H$_4$), one gram of polymethylhydrosiloxane (PS 120, 30 ctsks, available from Petrarch Systems, Inc., Levittown, PA), and 40 grams of methyl ethyl ketone. This solution was sponge dabbed onto the dressing material until a coating of the desired weight percent was formed. The methyl ethyl ketone was allowed to evaporate and the material was cured at 80° C. for ten minutes. The final composition of the dressing was 73.3% Sephadex ® G-25-80, 18.3% PTFE, and 8.4% silicone coating.

The dressing material, which had a chamois-like appearance and feel, was then cut into 5 cm×5 cm squares, packaged, and sterilized. Two or three squares were used for testing the physical characteristics of the dressings.

The tensile strength of the dressings was measured according to ASTM 638. The measurements were made on strips of material cut parallel to the longitudinal axis of the final calendering step. The tensile strength was about 300 psi (2 megapascals). A tensile strength in the range of 20 to 1000 psi can be obtained by variation of the preparation procedures.

The water vapor permeability of the dressing was measured according to ASTM E 96-66, Procedure B, at 23° C. with an 81% relative humidity gradient across the dressing. A 5.7 cm$^2$ area of dressing was evaluated.

The data showed that the permeability of the test dressings was 400 grams H₂O/m²/24 hours.

The rate of evaporative water loss was determined according to ASTM E 96-66, Procedure BW, at 23° C. with a 100% relative humidity gradient across the test dressing material. The rate of evaporative water loss was found to be $2 \times 10^3$ gm H₂O/m²/24 hrs.

To determine the water absorption, small pieces of dressing material (0.1 to 0.5 g) were weighed and placed in water for 2 hours. They were removed, blotted with a paper towel to remove non-absorbed water, and reweighed. The dressing materials absorbed 2.5 g H₂O per gram of dry dressing.

EXAMPLE 2-Evaluation of PTFE Composite Dressing on shallow wounds of pigs.

Three materials were tested.

Dressing A-PTFE composite material with Sephadex ® particulate filler coated on one side with silicone made by the method described in Example 1.

Dressing B-PTFE composite material with Sephadex ® filler, not coated. The PTFE composite material was made by the process of Example 1 to the exclusion of the coating process.

Control-Polyethylene film (natural grade, low density) 37.5 micrometers thick.

The dressings were double packed and sterilized by ethylene oxide gas followed by degassing (24 hours in an aerator).

The hair on the back of the pigs was clipped with electric clippers 48 hours prior to the start of the surgical procedure. Protective guards were put on the animals at this time. At the start of the procedure, the anaesthetised pigs were shaved, taking care not to damage the skin. Sterile techniques were used throughout the procedure and all operatives wore masks, hats, sterilized gowns and gloves. Care was taken to rinse any glove powder from the gloves.

Twelve standard shallow wounds, each measuring 2.5 cm×2.5 cm, were made on each animal using sharp round-bellied scalpel blades. The scalpel was held in the plane of the skin and the epidermis and papillary layer of the dermis were cut away. When all 12 wounds had been made, the dressings were applied. Four wounds were covered with dressing A, four with B, and four with the control.

Biopsy specimens were obtained after one, three, and six days from each of the 12 wounds. Using a template measuring approximately 1 cm×4 cm, cuts were made through the dressing to the wound surface and extended the full thickness of the skin. The specimens were placed in 10% buffered formal saline.

After 24 hours fixation the biopsy specimens were trimmed to yield four blocks. For each wound, two of the blocks spanning the entire width of the wound were embedded in wax and serial sections prepared using a rotary microtome set to cut at 10 microns. Every fifth section was mounted on glass slides to provide a series of sections for staining with H & E, Weigert and van Geison's stain and Masson's trichrome method.

Sections were examined under the microscope and the wound surfaces of the control and Sample A and B dressings were compared.

RESULTS

Day 1

Polyethylene Film Control Dressing: All four wounds that had been covered with the polyethylene film control dressing were similar. There was a fibrinous exudate on the cut surface of the dermis which was approximately 0.1 mm thick. The exudate appeared to be hydrated because there were no signs of damage by dehydration. The exudate contained moderate numbers of erythrocytes and cells characteristic of the acute inflammatory response; polymorphonuclear leucocytes, monocytes and eosinophils. Near the surface, just below the dressing, many of the polymorphs were "stringy" and pycnotic indicating that they were dying. In the dermis the small superficially placed blood vessels were dilated and the perivascular connective tissue stroma was filled with cells similar to those seen in the exudate. The collagen bundles were moderately swollen, indicating some edema. There was some swelling of the epidermis at the margins of the wound, but no epidermal regeneration had yet taken place.

Dressing B: The four wounds treated with the PTFE/-Sephadex ® membrane without a silicone top coat were similar to one another. The dressing could be seen on the wound surface in the histological sections. It measured approximately 0.76 mm thick. Exudate penetrated only one-third of the way into the dressing. The Sephadex ® beads were about 80 microns in diameter and were enmeshed in a network of fine PTFE fibrils. Those beads towards the surface stained deeply blue with the basic haematoxylin stain. Beads in the region impregnated with exudate stained a much paler shade of blue. This may have indicated a difference in pH, the beads surrounded by exudate being more acid. The exudate filled the interstices of the membrane around all of the beads, confirming that the dressing had an open, porous structure. There were no cells in the exudate within the dressings and the exudate was homogenous under moderate magnification in the optical microscope and did not contain the fibrin network seen under the polyethylene dressing. For the most part, the dressing was directly on the cut surface of the dermis without an intervening layer of blood clot or exudate. There was no epidermal regeneration.

Dressing A: All four wounds treated with composite dressing A were similar. The dressings were in place on the wounds in the histological sections. The dressing was approximately 0.8 mm thick. The silicone layer was not present in the sections and was evidently dissolved away during processing. In contrast to dressing B, exudate filled all the interstices of the dressing almost to the surface. No cells had penetrated into the dressing beyond the first layer of open pores immediately adjacent to the wound surface. There was no fibrinous network. The dressing was in contact with the cut surface of the dermis. There were a few inflammatory cells—polymorphonuclear leucocytes, monocytes and eosinophils—present at the dressing/wound interface and only very moderate numbers of these cells in the loose connective tissue stroma around small blood vessels in the wound. The Sephadex ® beads stained very faintly with haematoxylin as noted above. Epidermal regeneration had just begun and there was up to 0.3 mm of new epidermis around some hair follicles.

Day 3

Control Dressing: At the end of the third day there was a thick (approximately 0.5 mm) cellular exudate between the polyethylene dressings and the wounds. This contained numerous inflammatory cells, mostly polymorphonuclear leucocytes. The exudate was heavily infected with colonies of bacteria (cocci), especially at the wound margins and in places where the epidermis was most mature. Most of the cells in the exudate were dead or dying.

The wounds were almost entirely covered by newly regenerated epidermis. For the most part, it was lying on a layer of fibrinous exudate but in some places it was in direct contact with the dermis. The new epidermis was several cells thick and was differentiated into a basal cell layer, a middle layer of rounded cells and an upper layer of flattened cells with pycnotic nuclei. There was no differentiated horny layer. The epidermal-dermal border was undulating.

In the dermis there were still numerous polymorphonuclear leucocytes but the predominant cell was the mononuclear fibroblast. Blood vessel and connective tissue regeneration was just beginning beneath the new epidermis.

Dressing B: At the end of the third day the dressing did not contain any more exudate than on the first day; the exudate had penetrated only the lower third of the membrane. Between Day 1 and Day 3 the surface of the wound beneath the dressing dehydrated and formed a scab. This scab was about 0.25 mm deep and consisted of dried collagenous tissue impregnated with leucocytes. Epidermal regeneration was taking place, but only about 50% of the wound surface was covered by new epidermis migrating from cut hair follicles and from the margins of the wound beneath the scab. The new epidermis had a flat epidermal-dermal border and was only two or three cells thick.

There were few inflammatory cells in the underlying dermis. There were no signs of bacterial colony formation. Connective tissue repair had not yet begun.

Dressing A: Between the first and third day after wounding, a thin layer of exudate containing leucocytes had collected between the dressing and the wound surface. Epidermal regeneration was taking place and an estimated 80–90% of the wound was covered by new epidermis. The new epidermis was situated on the cut surface of the dermis and had ridges which interdigitated with the slightly uneven surface of the wound. The new epidermis was about eight cells thick and was differentiated into a basal layer of columnar cells, a middle layer of cuboidal cells which were progressively more flattened towards the surface, and a superficial layer of flattened cells with pycnotic nuclei.

In the dermis blood vessels and connective tissue, regeneration was just beginning under the new epidermis. There were no inflammatory cells and no signs of bacteria colony formation in the exudate.

Day 6

Control Dressing: Under polyethylene, the new epidermis was now well differentiated and was keratinizing. There was a layer of infected exudate and in some places micro-abcesses had formed, breaching the surface of the new epidermis. Exaggerated epidermal ridges were formed and connective tissue regeneration was taking place under the new epidermis.

Dressing B: Under this dressing epidermal cell migration had now covered the wound but the new epidermis was less mature than on the control wound. There were, however, no signs of infection.

Dressing A: With dressing A there had been no change in the dressing and there were no signs of infection. The epidermis was keratinizing and new connective tissue was developing under the epidermis. The epidermis was less hypertrophied than under the control dressing and there was less inflammation in the dermis. A few beads of Sephadex ® were embedded in the wound, but there were no adverse reactions associated with these inclusions.

Comparison of the results using the composite dressing with and without a covering of silicone to control the water vapor permeability clearly confirmed the validity of the hypothesis concerning the advantages of controlling the hydration of the wound by means of a properly designed dressing. The events within the dressings, as seen histologically, were interpreted to mean that both dressings initially absorbed the fluid blood and exudate present on the wound surface when the dressings were applied. It is known that because of the inflammatory reaction and increased vascular permeability, the wounds continue to ooze proteinaceous exudate for at least 24 hours after injury. Evidently, in the dressing lacking a silicone top coat, the exudate filling the lower third of the dressing soon dried, blocking the pores and preventing further uptake. Further loss of water vapor dehydrated the surface of the wound, damaging the exposed tissue and causing a scab to develop. In consequence, epidermal wound healing was delayed.

The opposite effect was seen under the occlusive polyethylene film control dressing. The exudate remained hydrated for at least three days, no scab formed, and the epidermis migrated through the moist exudate between the polyethylene film and the wound surface. Bacteria proliferated in the exudate and their presence stimulated an outpouring of leucocytes. The natural defense mechanisms were adequate to control the infection, but the presence of numerous bacterial colonies at three days in areas where the new epidermis prevented access of leucocytes to the infection, the occurrence of micro-abcesses at six days and the persistence of acute inflammation, indicated that this was a borderline septic situation. It is anticipated that the presence of more virulent organisms or a less adequate leucocytes response would result in septic wounds and delayed healing.

The condition of the wounds under those composite dressings which were provided with a silicone coating to control the water vapor permeability approached the ideal. The wound surface did not dry and epidermal regeneration was at least as rapid as under polyethylene. The perceived advantages compared with the control are that blood and exudate were absorbed, no gross infection developed and there was a remarkable reduction in inflammation. The epidermis migrated directly in contact with the injured dermis and, in consequence, the new epidermis was less hypertrophied on the sixth day.

Whereas under the occlusive polyethylene film dressing a mesh of fibrin was clearly seen in the exudate, no fibrin network was visible in the exudate within the composite dressing. This agrees with the findings of Åberg et al [Ålberg, M., Hedner, U., Jacobson, S. and Rothman, U., "Fibrinolytic Activity in Wound Secretion", *Scand. J. Plast. Recon. Surg.* 10, pp. 103-105 (1976)] that exudate absorbed by dextran polymer has high fibrinolytic activity.

It is concluded that the composite dressing that incorporated beads of dextran polymer in a matrix of polytetrafluoroethylene fibrils having a coating to control water vapor transmission provided beneficial effects on donor site wounds.

EXAMPLE 3

Two scalds were made, one on either side of the back of a young pig. The injury was created with running water at 80° C. applied for 35 seconds over a circular area of 16.6 cm². The dead epidermis was removed from the burns surfaces. Ten days later the eschar, which comprised the skin tissue which had been killed by scalding, was removed with a proteolytic enzyme preparation. Loose debris was scraped from the surface. The debrided burns were then treated with sterile composite dressings, i.e., sample A of Example 2—PTFE membrane with Sephadex ® particulate filler coated one side with silicone made by the method described in Example 1. The dressings were changed after 8 hours, 17 hours, 25 hours, 33 hours, 44 hours, and 56 hours after enzymatic debridement. The wounds were grafted after an additional 30 hours. Autografts were cut with an air-powered dermatome and were sutured in place on the wounds. The grafted burns were covered with povidone-iodine ointment (Betadine ®, Purdue Frederick Co., Norwalk, CT) on a pad of gauze secured to, a sheet of plastic adhesive film (Tegaderm ®, 3M) and polyvinylchloride foam (Microfoam, 3M), and held in place with adhesive tape (Blenderm ®, 3M). This dressing was changed after 2 days and replaced by Betadine ® gauze and Tegaderm ® which was left in place for a further 8 days by which time it was judged that the grafted wounds no longer required the protection of a dressing. The pig was sacrificed 14 days after grafting and biopsy specimens of the grafted burns were processed for microscopic examination.

On the right side of the wound, a 0.8 mm thick graft was healthy and was covered by an intact epidermis. The fibrous repair tissue beneath the graft was about 2 mm thick. There were a few birefringent foreign bodies embedded in the repair tissue which had provoked a giant cell reaction.

On the left side of the wound, there was a healthy graft about 1.0 mm thick with intact epidermis on the surface of repair tissue measuring about 1 mm deep. There was no abnormal inflammation or other adverse reactions. By histological criteria this was an ideal result.

These results indicated that the composite dressing was efficacious in preparing the surfaces of contaminated wounds to accept a skin graft.

EXAMPLE 4

Eighty grams of corn starch (Fisher Scientific Co.) were thoroughly mixed with 60 ml of water. Thirty ml of PTFE resin dispersion (Teflon ® 30B) were added, with mixing, to form a viscous solution. Then, 30 grams of corn starch were added slowly with vigorous mixing to form a thick paste. This paste was subjected to shear forces on a rubber mill operating at 50° C. until a solid cohesive mass formed. This mass was subjected to 10 cycles of 3-layer folding and rerolling at 90° as described in Example 1. It was then calendered, folded and recalendered also as described in Example 1. The final sheet of material was 0.6 mm thick. The composition of this material was 80.1% corn starch and 19.9% PTFE. The material was coated with polymeric films to control water vapor permeability as is described in Example 6, below.

EXAMPLE 5

Ten ml of PTFE resin dispersion (Teflon ® 30B) were added with mixing to 20 grams of polyethylene powder (Microthene ®-USI Industries). The dough-like mixture which resulted was milled and calendered as described in Example 1. The final product was 0.15 mm thick. The composition of this material was 31.2% PTFE and 68.8% polyethylene. The material was hydrophilic due to the presence of residual surfactant from the PTFE dispersion, but after a thorough rinsing in distilled water, it became hydrophobic and would not absorb water or be wet by water.

EXAMPLE 6

Samples of composite dressing materials composed of PTFE-Sephadex ®, PTFE-Corn Starch and PTFE-Polyethylene mixtures were prepared by the procedures disclosed in Examples 1, 4, and 5, respectively. These uncoated dressings were then coated with semi-occlusive polymeric films with a variety of water vapor permeabilities. The coated dressings were used in animal trials to determine the useful range of dressing water vapor permeabilities and to establish a correlation between the in vitro permeability and in vivo water loss rates.

Three samples were prepared as follows:

Dressing C-PTFE Sephadex ® composite material was prepared as described in Example 1 exclusive of the silicone coating procedure. The final composition was 19.4% PTFE and 80.6% Sephadex ® G-25-80 and was 0.4 mm thick.

Dressing D-PTFE-Corn Starch material was prepared according to Example 4. The final composition was 20% PTFE and 80% Corn Starch and was 0.6 mm thick.

Dressing E-PTFE-Polyethylene material was prepared according to Example 5. The final composition was 20% PTFE and 80% polyethylene and was 0.150 mm thick.

These composite dressings were then coated according to one of the following procedures:

1-A 28.0 micron thick sheet of polyurethane (Estane ®, B. F. Goodrich), coated with an acrylate pressure sensitive adhesive was pressed onto the upper surface of the composite dressing material.

2-A 50 micron thick sheet of poly(dimethyl, diphenyl) siloxane was coated on its upper surface with a 30 micron film of 1:1 (by weight) mixture of Type A Silastic Medical Adhesive (Dow Corning) and toluene. The composite dressing material was applied to this surface and the adhesive was allowed to cure overnight at room temperature.

3-A 23 micron sheet of polyurethane (Estane ®) was coated on one surface with a 30 micron film of a 1:1 mixture (by weight) of Type A Silastic Medical Adhesive (Dow Corning) and toluene. The composite dressing material was pressed onto this surface and the adhesive was allowed to cure overnight at room temperature.

4-A 168 micron film of a 2:1 mixture (by weight) of Type A Silastic Medical Adhesive and toluene was cast onto a Teflon ® (Dupont) surface. After five minutes a piece of composite dressing material was pressed onto the adhesive film. After curing overnight, the composite dressing with an adherent silicone film was removed from the Teflon ® surface. The thickness of the silicone film is estimated at 112 microns.

5-This procedure is identical to Procedure 4, except a 135 micron film of a 1:1 mixture (by weight) of Type A Silastic Medical Adhesive (Dow Corning) and toluene was initially cast onto the Teflon ® surface. The thickness of the resulting silicone film is estimated at 68 micron.

6-This procedure is identical to Procedure 4, except a 102 micron film of a 1:1 mixture (by weight) of Type A Silastic Medical Adhesive (Dow Corning) and toluene was initially cast onto the Teflon surface. The thickness of the resulting silicone film is estimated at 51 micron.

Permeability of water vapor was measured in vitro through the dry dressings according to ASTM Method E96 Procedure B with these exceptions:

(a) a 4.9 cm$^2$ area of dressing was exposed
(b) the incubation temperature was 37°±1° C.
(c) the relative humidity of the incubation chamber was held at 24±2%.

Permeability of water vapor through the dressings when wetted and in contact with liquid water was measured according to ASTM Method E96 Procedure BW with the exceptions a, b, and c above. These results are reported in TABLE I.

Dressing squares (5 cm × 5 cm) were packaged, sterilized and handled as described in Example 1. Twelve dressing samples, with various compositions as shown in TABLE I, were used to cover twelve wounds on each of two pigs. Details of the animal trials were as described in Example 2. The actual rates of water vapor loss from the various dressings on the shallow wounds were determined at one day and three days after application with an evaporimeter (Model Ep1, Servo Med AB, Stockholm, Sweden). Results are reported in TABLE I.

Wound healing was measured as the percentage of the wound surface recovered with epidermal cells (Winter, G. D. 1972. In: Epidermal Wound Healing, H. Maibach and D. T. Rovee, eds. Chicago: Yearbook Medical Publishers). Data is recorded in TABLE I.

TABLE I*

| | DM** | CP** | Water Vapor Permeability, In Vitro E96 Proc. B | Water Vapor Permeability, In Vitro E96 Proc. BW | In Vivo Rate of Water Loss One Day | In Vivo Rate of Water Loss Three Days | PE** |
|---|---|---|---|---|---|---|---|
| 1 | C | 1 | $0.74 \times 10^3$ | $1.23 \times 10^3$ | $0.58 \times 10^3$ | $0.46 \times 10^3$ | 73 |
| 2 | C | 2 | — | $0.87 \times 10^3$ | $0.45 \times 10^3$ | $0.38 \times 10^3$ | 64 |
| 3 | C | 3 | — | $2.00 \times 10^3$ | $0.92 \times 10^3$ | $0.77 \times 10^3$ | 66 |
| 4 | C | 4 | $1.02 \times 10^3$ | $1.34 \times 10^3$ | $0.69 \times 10^3$ | $0.53 \times 10^3$ | 79 |
| 5 | C | 5 | $0.82 \times 10^3$ | $2.64 \times 10^3$ | $0.96 \times 10^3$ | $0.73 \times 10^3$ | 67 |
| 6 | C | 6 | $1.40 \times 10^3$ | $3.57 \times 10^3$ | $1.10 \times 10^3$ | $0.74 \times 10^3$ | 71 |
| 7 | D | 1 | $0.95 \times 10^3$ | $0.94 \times 10^3$ | $0.49 \times 10^3$ | $0.43 \times 10^3$ | 89 |
| 8 | D | 2 | — | $0.83 \times 10^3$ | $0.41 \times 10^3$ | $0.38 \times 10^3$ | 81 |
| 9 | D | 3 | — | $2.56 \times 10^3$ | $0.90 \times 10^3$ | $0.82 \times 10^3$ | 75 |
| 10 | D | 4 | $1.35 \times 10^3$ | $1.54 \times 10^3$ | $0.67 \times 10^3$ | $0.58 \times 10^3$ | 71 |
| 11 | D | 6 | $2.33 \times 10^3$ | $4.10 \times 10^3$ | $1.16 \times 10^3$ | $1.03 \times 10^3$ | 72 |
| 12 | E | None | $3.06 \times 10^3$ | $1.67 \times 10^4$ | $2.12 \times 10^3$ | $1.79 \times 10^3$ | 39 |

*All values in units of gm $H_2O/m^2/24$ hours.
**DM—dressing material
DP—coating procedure
PE—percent epithelization after three days The water vapor permeabilities measured by ASTM Method E96 Procedure BW (the wet dressing method) compared with the in vivo rate of water loss at one day showed that there was a definite correlation between the in vitro and in vivo measurements. Water vapor permeabilities measured by procedure BW were superior to those measured by ASTM Method E96, Procedure B, in predicting in vivo performance.

Also, as shown in Table I, all dressings having a coating permitted wound healing to progress to at least 64% in three days whereas wound healing under the uncoated dressing was no more than 39% in the same time. A dried, fibrous surface to the wound was observed under the uncoated dressing. Histological observations of the wound under the uncoated dressing were similar to those of Dressing B at 3 days of healing previously reported in Example 2. The histological appearance of all other wounds, i.e., those under coated dressings, were similar to those of Dressing A at 3 days of healing reported in Example 2.

EXAMPLE 7

Samples of composite dressing materials were prepared from mixtures of PTFE (Teflon 30B) and various hydrophilic particulate materials, according to the procedures disclosed in Example 1. TABLE II contains the amounts of particulate material, water and PTFE used in each mixture. The thickness of the dressings varied from 0.1 mm to 2.0 mm. All dressings were useful in the practice of the present invention.

TABLE II

| Particle Material | Weight of Particulate | Volume of Water | Volume Teflon ® 30B$^{(i)}$ | Composition of Product (Dried) |
|---|---|---|---|---|
| Chitosan$^{(a)}$ | 40.0 gm | 80. ml | 15. ml | 25% PTFE, 75% Chitosan |
| Alginic Acid$^{(b)}$ | 60.0 gm | 120. ml | 25. ml | 27.5% PTFE, 72.5% Alginic Acid |
| Collagen$^{(c)}$ | 8.0 gm | 8. ml | 4. ml | 31% PTFE, 69% Collagen |
| Kaolin$^{(d)}$ | 85.0 gm | 50. ml | 30. ml | 24% PTFE, 76% Kaolin |
| Kaolin - Derivatized | 50.0 gm | 100. ml | 30. ml | 21% PTFE, 39.5% Kaolin |

TABLE II-continued

| Particle Material | Weight of Particulate | Volume of Water | Volume Teflon ® 30B[i] | Composition of Product (Dried) |
|---|---|---|---|---|
| Starch[e] | of each | | | 39.5% Derivatized Starch |
| Sepharose ®[f] | 20.0 gm | 140. ml | 10. ml | 31% PTFE, 69% Sepharose |
| Cellulose[g] | 20.0 mg | 20. ml | 10. ml | 31% PTFE, 69% Cellulose |
| Diethyl Amino Ethyl Sephadex[h] | 10.0 gm | 150. ml | 20. ml | 64.5% PTFE, 35.5% Diethyl Amino Ethyl Sephadex |
| Calcium Carbonate | 30.0 gm | 20. ml | 15. ml | 31% PTFE, 69% Calcium Carbonate |

[a]Chitosan - Kytex M, Hercules
[b]Alginic Acid - Type III, Sigma Chem. Co.
[c]Collagen - purified from rat-tail tendon
[d]Kaolin - Kaopaque
[e]Derivatized Starch - SGP 5125, General Mills Chemicals
[f]Sepharose ® - Type 4B-200, Sigma Chem. Co.
[g]Cellulose - Microcrystalline, Type 20, Sigma Chem. Co.
[h]Diethyl aminoethyl Sephandex ® - A-50-120, Sigma Chem. Co.
[i]Polytetrafluoroethylene - Teflon ® 30B, Dupont

EXAMPLE 8

Samples of composite dressing materials containing various medicaments which may promote wound healing, reduce wound infection or be hemostatic were prepared according to the procedures disclosed in Example 1. The compositions of these dressings are presented in TABLE III. The medicaments were introduced into the dressings by three methods. Method A-Medicaments were added to the PTFE-particulate mixture before fibrillation of the PTFE on the two roll mill, thus ensuring the medicaments were thoroughly enmeshed in the fibrillated PTFE matrix. Method B-The fully manufactured dressing sample was soaked in an aqueous solution of medicament, allowing the sample to absorb medicament and then was dried, trapping the medicament in the sample. Method C-A solution of medicament was coated onto the surface of the sample and then allowed to dry.

TABLE III

| Dressing Composition | Medicaments | Preparation Procedure |
|---|---|---|
| PTFE 24.3% Sephadex ® G-25-80 72.9% | Ascorbic Acid 2.0% Boric Acid 0.4% Aluminum Acetate 0.4% | Method A |
| PTFE 20.0% Sephadex ® G-25-80 79.8% | Neomycin Sulfate 0.2% (antibacterial) | Method B |
| PTFE 20% Sephadex ® G-25-80 80% | Nystatin (antifungal) | Method C - An aqueous solution containing 100,000 units was coated onto the dressing surface and allowed to dry. |
| PTFE 21% Kaolin 39.5% SGP 5125 Derivatized Starch 39.5% | Iodine (antibacterial) | Method B - Soaked in 0.5% KI$_3$ aqueous solution. Material turned characteristic gun-metal blue. |
| PTFE 25% Chitosan 75% | Chitosan (hemostatic agent) | Method A |
| PTFE 20% Sephadex ® G-25-80 | Povidone Iodine | Method B - The dressing was soaked in a 10% Povidone-Iodine solution and dried. |

The data show that all of the dressings were useful in treatment of wounds.

Various modifications and alterations of this invention will become apparent to those skilled in the art without departing from the scope and spirit of this invention, and it should be understood that this invention is not to be unduly limited to the illustrative embodiments set forth herein.

What we claim is:

1. A composite wound-dressing which is a sheet material, comprising:
   (a) a polytetrafluoroethylene fibril matrix,
   (b) 0.5 to 10 parts of hydrophilic absorptive particles per part of PTFE by weight enmeshed in said matrix, the absorptive particles having absorptive capacity greater than 0.5 grams of water per gram of dry particles, and
   (c) a partially occlusive film coated on one surface of said matrix,
   wherein substantially all of said hydrophilic absorptive particles are unavailable for sloughing.

2. The composite wound-dressing according to claim 1 wherein said hydrophilic absorbent particles are alginic acid, polyacrylatecellulose graft copolymer, collagen, chitin, chitosan, dextran, clay, casein, zein, carboxymethyldextran, starch, hydroxyethyl starch, hydrolyzed polyacrylonitrile, starch-methacrylonitrile polymer, polyacrylamide, hydrolyzed polyacrylamide, cellulose, carboxymethylcellulose or derivatives or mixtures thereof.

3. The composite wound-dressing according to claim 1 wherein said hydrophilic absorptive particles are particles of a crosslinked dextran derivative.

4. The composite wound-dressing according to claim 1 wherein said hydrophilic absorptive particles are admixed with inert diluent particles.

5. The composite wound-dressing according to claim 4 wherein said inert diluent particles are selected from polyethylene, polypropylene, polystyrene, kaolin, talc, silica, bentonite, and vermiculite.

6. The composite wound-dressing according to claim 4 wherein said particles comprise 40-90% of the weight of the said composite wound-dressing.

7. The composite wound-dressing according to claim 4 wherein said particles comprise about 80 to 90% of the weight of said composite wound-dressing.

8. The composite wound-dressing according to claim 1 wherein said hydrophilic absorbent particles range in size from about 0.1 to 300 micrometers.

9. The composite wound-dressing according to claim 1 wherein said hydrophilic absorbent particles range in size from about 1.0 to 80 micrometers.

10. The composite wound-dressing according to claim 1 wherein said fibril matrix comprises fibrils having a thickness in the range of about 0.025 to 0.5 micrometers.

11. The composite wound-dressing according to claim 1 wherein said partially occlusive film is a polymer of silicone, urethane, or acrylate.

12. The composite wound-dressing according to claim 1 wherein the rate of transmission of moisture through said dressing is in the range of about 240 to 2400 g/m$^2$/24 hrs, at 37° C. and 75% relative humidity.

13. The composite wound-dressing according to claim 1 wherein said dressing has a thickness in the range of 0.1 to 10 mm.

14. The composite wound-dressing according to claim 1 wherein said partially occlusive film has a thickness in the range of 2 to 200 micrometers.

15. The composite wound-dressing according to claim 1 further comprising medicaments selected from antibacterial agents, antifungal agents, hemostatic agents, and wound-healing agents.

16. A method of treating a wound comprising applying to said wound a composite wound-dressing which is a sheet material comprising:
 (a) a polytetrafluoroethylene fibril matrix; and
 (b) 0.5 to 10 parts of hydrophilic absorptive particles per part of PTFE by weight enmeshed in said matrix, the absorptive particles having absorptive capacity greater than 0.5 grams of water per gram of dry particles, wherein substantially all of said hydrophilic absorptive particles are unavailable for sloughing.

17. The method of treating a wound according to claim 16 wherein said wound-dressing further comprises a partially occlusive film coated on one surface of said matrix.

18. The method of treating a wound according to claim 16 wherein said wound-dressing further comprises medicaments selected from antibacterial agents, antifungal agents, hemostatic agents, and wound-healing agents.

* * * * *